United States Patent
Galea et al.

(10) Patent No.: US 10,207,101 B2
(45) Date of Patent: Feb. 19, 2019

(54) SYSTEM AND METHOD FOR SUPPRESSING VESTIBULAR ACTIVITY OF A HUMAN SUBJECT

(71) Applicants: Vivonics, Inc., Bedford, MA (US); Mayo Foundation For Medical Education and Research, Rochester, MN (US)

(72) Inventors: Anna M Galea, Stow, MA (US); Michael J. Cevette, Cave Creek, AZ (US); Gaurav N. Pradhan, Fountain Hills, AZ (US); Jan Stepanek, Scottsdale, AZ (US); Daniela Cocco, Phoenix, AZ (US); Sarah Oakley Holbert, Phoenix, AZ (US); Linsey S. Scheibler, Universal City, TX (US); Jamie M. Bogle, Scottsdale, AZ (US)

(73) Assignees: Vivonics, Inc., Bedford, MA (US); Mayo Foundation For Medical Education and Research, Rochester, MN (US)

( * ) Notice: Subject to any disclaimer, the term of this patent is extended or adjusted under 35 U.S.C. 154(b) by 0 days.

(21) Appl. No.: 15/079,445

(22) Filed: Mar. 24, 2016

(65) Prior Publication Data
US 2017/0274211 A1   Sep. 28, 2017

(51) Int. Cl.
*A61N 1/36* (2006.01)
*A61N 1/20* (2006.01)
*A61N 1/04* (2006.01)

(52) U.S. Cl.
CPC ....... *A61N 1/0456* (2013.01); *A61N 1/36034* (2017.08); *A61N 1/36036* (2017.08); *A61N 1/20* (2013.01)

(58) Field of Classification Search
CPC ..... A61N 1/36032; A61N 1/20; A61N 1/0456
See application file for complete search history.

(56) References Cited

U.S. PATENT DOCUMENTS

| 6,212,432 B1 * | 4/2001 | Matsuura ............. A61N 1/32 607/50 |
| 8,630,714 B1 * | 1/2014 | Webb ............. A61N 1/0464 607/51 |
| 9,564,059 B2 | 2/2017 | Cevette et al. |
| 2002/0026219 A1 | 2/2002 | Collins et al. |
| 2006/0149337 A1 | 7/2006 | John |
| 2010/0114255 A1 | 5/2010 | Chan et al. |

(Continued)

OTHER PUBLICATIONS

Written Opinion of the International Searching Authority, dated Jun. 6, 2017 in International Application No. PCT/US2017/016694, seven (7) pages.

(Continued)

*Primary Examiner* — Mark Bockelman
(74) *Attorney, Agent, or Firm* — Iandiorio Teska & Coleman, LLP

(57) ABSTRACT

A system for suppressing vestibular activity of a human subject includes an electronics module configured to generate one or more electrical stimulation signals. A plurality of electrodes each placed proximate a predetermined location on a head of a human subject is configured to deliver the one or more electrical stimulation signals to the predetermined location to suppress vestibular activity of the human subject.

30 Claims, 13 Drawing Sheets

(56) References Cited

U.S. PATENT DOCUMENTS

2011/0029045 A1* 2/2011 Cevette ............... G09B 9/00
 607/62
2016/0007921 A1 1/2016 Galea et al.

OTHER PUBLICATIONS

A.R. Fregly, "Vestibular Ataxia and its Measurement in Man", In HH Kornhuber (Ed.), Handbook of Sensory Physiology, Chapter V, Vestibular System Part 2: Psychophysics, Applied Aspects and General Interpretations. New York: Spring-Verlag ed. 1974, (one (1) cover sheet and pp. 321-360).

Draper et al., "Effects of Image Scale and System Time Delay on Simulator sickness Within Head-Coupled Virtual Environments", Human Factors, vol. 43, No. 1, Spring 2001, pp. 129-146.

David M. Johnson, "Simulator Sickness During Emergency Procedures Training in a Helicopter Simulator: Age, Flight Experience, and Amount Learned", Technical Report 1211, U.S. Army Research Institute for the Behavioral and Social Sciences, Sep. 2007, (sixty-six (66) pages total).

Kennedy et al., "Simulator Sickness Is Polygenic and Polysymptomatic: Implications for Research", The International Journal of Aviation Psychology, 2(1), 1992, Lawrence-Erlbaum Associates, Inc., pp. 23-38.

Kennedy et al., "Simulator Sickness, Ch. 15", Motion and Space Sickness, George H. Crampton, Editor, CRC Press, Inc., 1990, pp. (two (2) cover sheets and pp. 317-341).

Eugenia M. Kolasinski, "Simulator Sickness in Virtual Environments", Technical Report 1027, U.S. Army Research Institute for the Behavioral and Social Sciences, May 1995, (sixty-eight (68) pages total).

Webb et al., "Simulator Sickness in a Helicopter Flight Training School", Aviation, Space, and Environmental Medicine, vol. 80, No. 6, Jun. 2009, pp. 541-545.

Claude A. Claremont, "The Psychology of Sea-Sickness", Psyche, vol. 11, 1931, (one (1) cover sheet and pp. 86-90).

* cited by examiner

SYSTEM AND METHOD FOR SUPPRESSING VESTIBULAR ACTIVITY OF A HUMAN SUBJECT

GOVERNMENT RIGHTS

This invention was made with government support under No. W56HZV-13-C-0036, awarded by the U.S. Army. The government has certain rights in the invention.

FIELD OF THE INVENTION

This invention relates to a system and method for suppressing vestibular activity of a human subject.

BACKGROUND OF THE INVENTION

The ability to maintain spatial orientation and balance is the result of an elaborate synchronization of neural inputs from the vestibular, visual, and proprioceptive systems. When there is a mismatch among these signals or when input patterns from different senses do not correspond to stored expected sensory patterns, spatial disorientation may occur. The two primary conflicts occur between the visual and vestibular senses (i.e., intersensory conflict) and within the vestibular sense between the semicircular canals and otoliths (i.e., intrasensory conflict). Secondary conflict, however, may come from proprioceptive inputs that fail to synchronize with other sensory cues, particularly visual and peripheral proprioceptors connected to the vestibular system through vestibulospinal pathways. This creates the sensation commonly known as Motion Sickness. It includes a range of symptoms, from nausea and salivation to a sensation of warmth, tiredness, and other cognitive symptoms. In addition, sensory conflicts remain one of the most persistent issues facing advanced flight simulation development. Flight simulators have been shown to improve training effectiveness with considerably lower cost and risk than actual flight training. The capability to use simulation in training brings advantages in acquisition of skill sets, development of competencies, the reduction of errors in real environments, and decreased costs. The simulation environment, however, imposes limitations in matching real world sensory experiences. These limitations may manifest in the form of simulator-induced motion sickness, also known as simulator sickness (SS). SS is a variant of motion sickness resulting from exposure to simulated environments such as flight simulators, driving simulators and similar virtual, immersive environments. Whereas motion sickness refers to the adverse consequences of exposure to environments that physically put an individual in motion, SS is mainly the result of technological limitations in simulating dynamic environments that create a conflict in the body's self-motion perception sensors. Because of the wide variety of these symptoms, such as nausea, oculomotor disorders, disorientation, and the like, SS has also been described as "polygenic" since several factors have been identified including age, gender, simulator features, e.g., lag and field of view (FOV), and factors associated with the task performed, e.g., duration and degree of control. The theory of sensory conflict, also known as the sensory rearrangement or neural mismatch theory, indicates that sickness occurs when the pattern of inputs from different senses and within a single sensory modality do not correspond to the stored patterns of such inputs based on past experience, as a result of both cognitive and perceptual discrepancy. When SS symptoms develop, the value of the training experience and data derived during the experience may be compromised and in the most extreme cases results in negative transfer-of-training. Moreover, since symptoms may persist or recur spontaneously up to one day after exposure, various training centers routinely ground pilots for 6 to 24 hours after simulator time. These factors can lower the acceptance and overall utility of simulator enhanced learning. Conventional preventative pharmacological agents commonly used for motion sickness are typically ineffective to prevent SS and may be commonly associated with significant side effects after the simulated sessions including drowsiness and fatigue. Thus, simulator design may have a significant role in decreasing the incidence of SS. However, even with technological advances, imperfections including optical deficiencies, image scale factor magnifications, system time delays, limited field of view (FOV) displays head tracker inaccuracies, and the like, still remain unsolved limitations which contribute to SS.

Thus there is a need to mitigate motion sickness and/or SS by reducing or eliminating the mismatch between sensory cues inputs expected by a human subject and improve simulation based training.

SUMMARY OF THE INVENTION

In one aspect, a system for suppressing vestibular activity of a human subject, the system is featured. The system includes an electronics module configured to generate one or more electrical stimulation signals. A plurality of electrodes each placed proximate a predetermined location on a head of a human subject is configured to deliver the one or more electrical stimulation signals to the predetermined location to suppress vestibular activity of the human subject.

In one embodiment, the system plurality of electrodes may be bi-laterally placed on opposing sides of the head. The predetermined location may include a mastoid process, the ear, or a temporal bone of the human subject. The one or more electrical stimulation signals may include one or more direct current (DC) signals. The one or more stimulation signals may include one or more DC signals each with an imposed carrier wave. The one or more stimulation signals may include one or more alternating current (AC) signals. The one or more electrical stimulation signals may be configured to hyperpolarize and/or depolarized cells located at each predetermined location to create a desired induced perception of motion. The plurality of electrodes may be configured to deliver electrical stimulation to suppress the vestibular system of the human subject to actual motion such that perception of motion of the human subject is reduced. The suppression of the vestibular system of the human subject to actual motion may decrease motion sickness that may arise from motion sensed by the human subject. The plurality of electrodes may include a first pair of electrodes placed on one side of the head of the human subject at the predetermined location, another pair of electrodes placed on an opposite side of the head of the human subject at the predetermined location, and a ground electrode placed on the head or neck of the human subject. Each pair of electrodes may include an electrode configured as positive electrode and an electrode configured as a negative electrode. The one or more electrical stimulation signals may be configured as one or more DC signals applied to each positive and negative electrode such that the one or more DC signals are transmitted from the positive electrode located at high predetermined location on the head of the human subject to the negative electrode located at a low location on the head of the human subject to suppress vestibular activity.

The high predetermined location may include a high location on a mastoid process of the human subject and the low location includes a low location on mastoid process of the human subject. The one or more electrical stimulation signals may be configured as one or more DC signals each imposed carrier wave applied in phase to each positive and negative electrode such that the one or more DC signals with the imposed carrier waves are transmitted from the positive electrode at a high predetermined location to the negative electrode at a low predetermined location to suppress vestibular activity. The one or more electrical stimulation signals may be configured as one or more DC signals each imposed carrier wave applied temporally offset to each positive and negative electrode such that the one or more DC signals with the imposed carrier waves are transmitted from the positive electrode at a high predetermined location on one side of the head to the negative electrode at a low predetermined location on an opposite side of the head to suppress vestibular activity. The high predetermined location may include a high location on mastoid process and the low predetermined location includes a low location on mastoid process of the human subject. The plurality of electrodes may include one electrode placed on one side of the head of the human subject at the predetermined location and another electrode is placed on an opposite side of the head of the human subject at the predetermined location. The one or more electrical stimulation signals may be configured as one or more AC signals applied to the electrode placed on one side of the head and the electrode placed on one the opposite side of the head such that the one or more AC signals are transmitted back and forth from one electrode at its maximum current at the predetermined location on one side of the head to the another electrode at its maximum negative current at the predetermined location on an opposite side of the head of the human subject to suppress vestibular activity.

In another aspect, a method for suppressing vestibular activity of a human subject is featured. The method includes generating one or more electrical stimulation signals, and delivering the one or more electrical stimulation signals to a plurality of electrodes each placed proximate a predetermined location on a head of the human subject such that the one or more electrical stimulation signals suppress vestibular activity of the human subject.

In one embodiment, the method may include bilaterally placing the electrodes on opposing sides of the head of the human subject at the predetermined location. The one or more electrical stimulation signals may hyperpolarize and/or may depolarize cells located at each predetermined location to create a desired induced perception of motion. The method may include delivering electrical stimulation to suppress the vestibular system of the human subject to actual motion such that perception of motion of the human subject is reduced. The suppression of the vestibular system of the human subject to actual motion may decrease motion sickness that may arise from motion sensed by the human subject. The one or more electrical stimulation signals may include one or more direct current (DC) signals. The one or more stimulation signals may include one or more DC signals each with an imposed carrier wave. The one or more stimulation signals may include one or more alternating current (AC) signals. The one more electrical stimulation signals may include one or more DC signals transmitted from a positive electrode at a high predetermined location on one side of the head to the negative electrode at a low predetermined location on an opposite side of the head to suppress vestibular activity. The one more electrical stimulation signals may include one or more DC signals with the imposed carrier waves transmitted in phase from a positive electrode at a high predetermined location on one side of the head to the negative electrode at a low predetermined location on an opposite side of the head to suppress vestibular activity. The one more electrical stimulation signals may include one or more DC signals with the imposed carrier waves transmitted temporally offset from a positive electrode at a high predetermined location on one side of the head to the negative electrode at a low predetermined location on an opposite side of the head to suppress vestibular activity. The one more electrical stimulation signals may include one or more AC signals transmitted from an electrode on one side of the head at the determined location to an electrode on an opposite side of the head to suppress vestibular activity.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Figure 1:
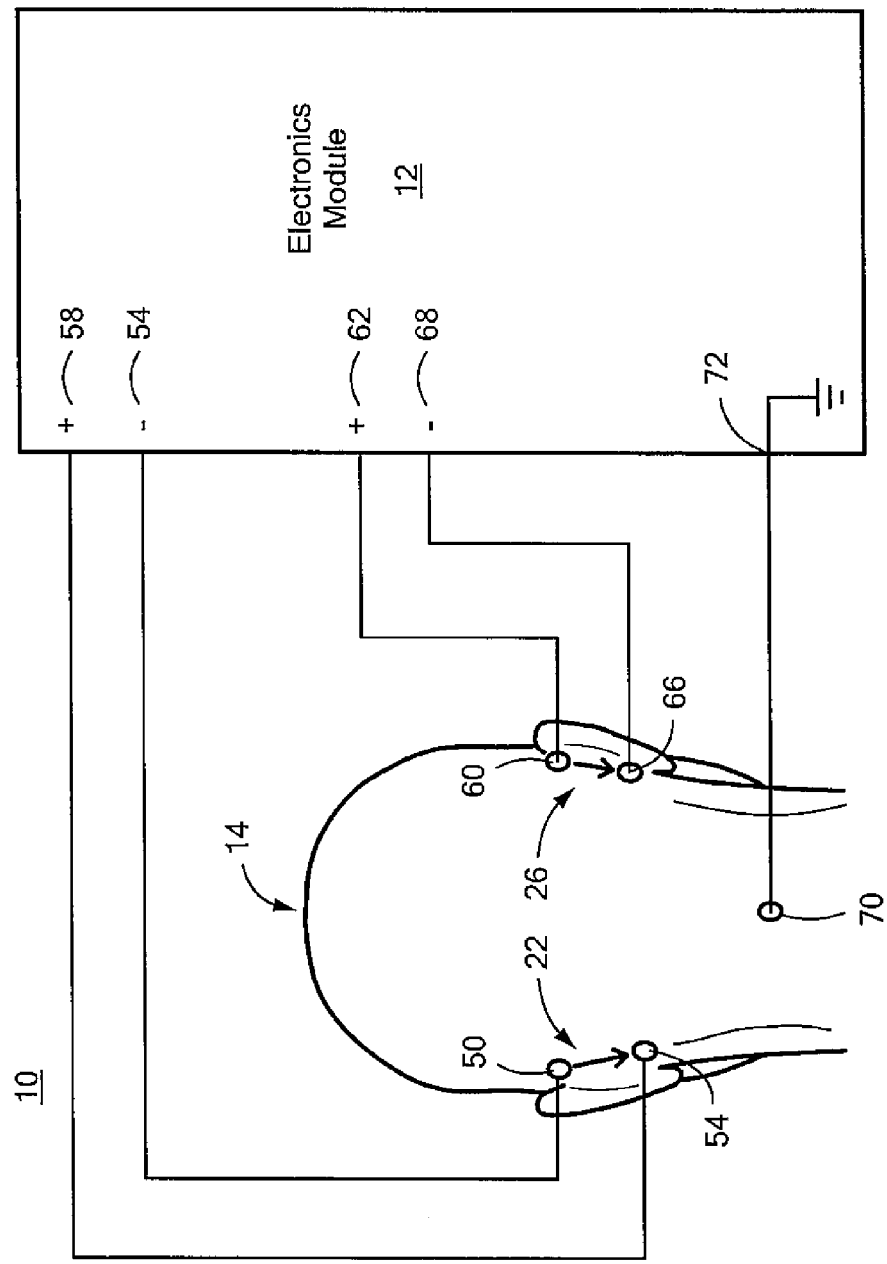
FIG. 1 is a schematic block diagram showing the primary components of one embodiment of the system for suppressing vestibular activity of a human subject of this invention.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

Figure 2:
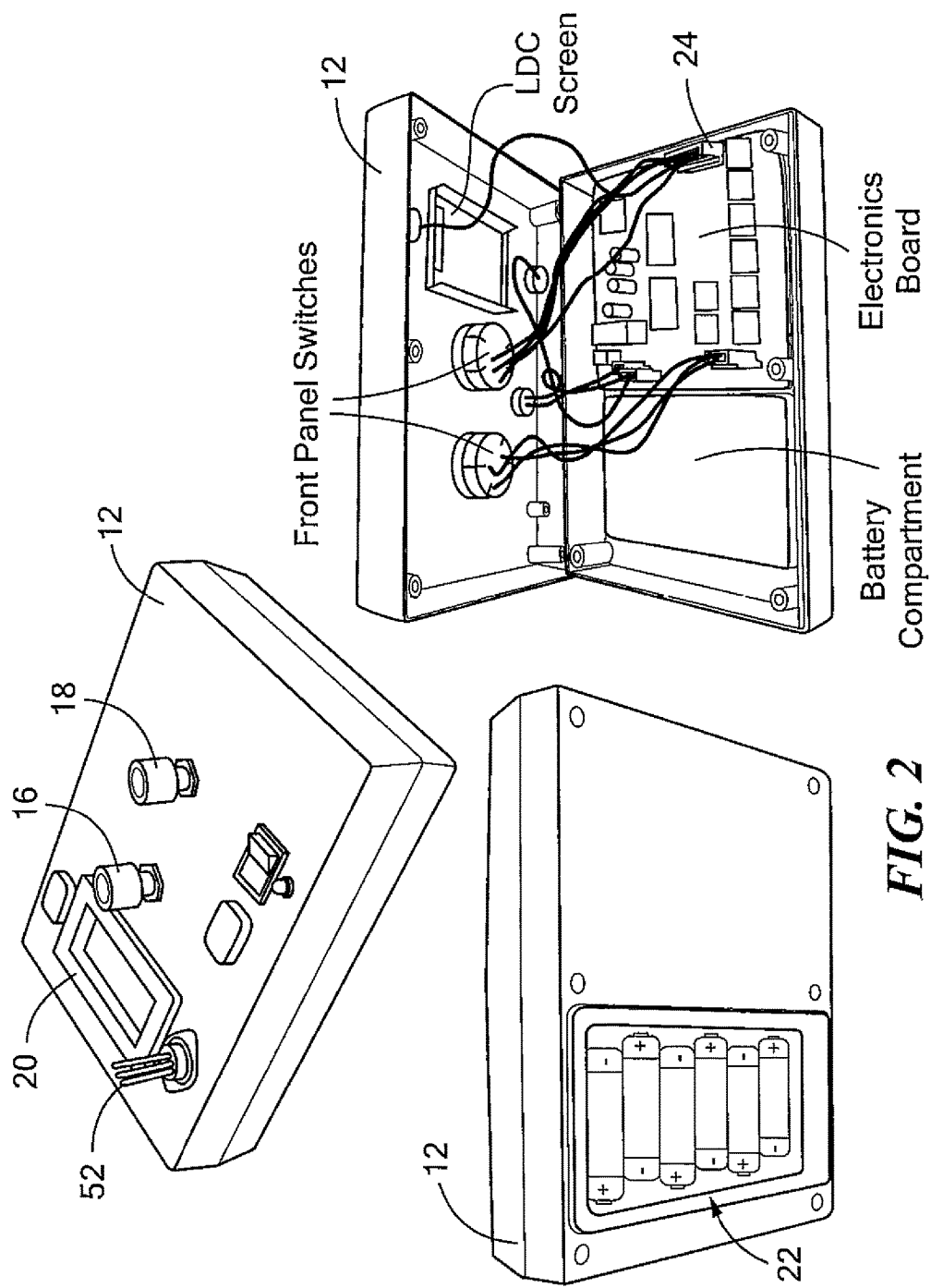
FIG. 2 shows in further detail the primary components associated with one embodiment of the electronics module shown in FIG. 1.
Figure 3A:
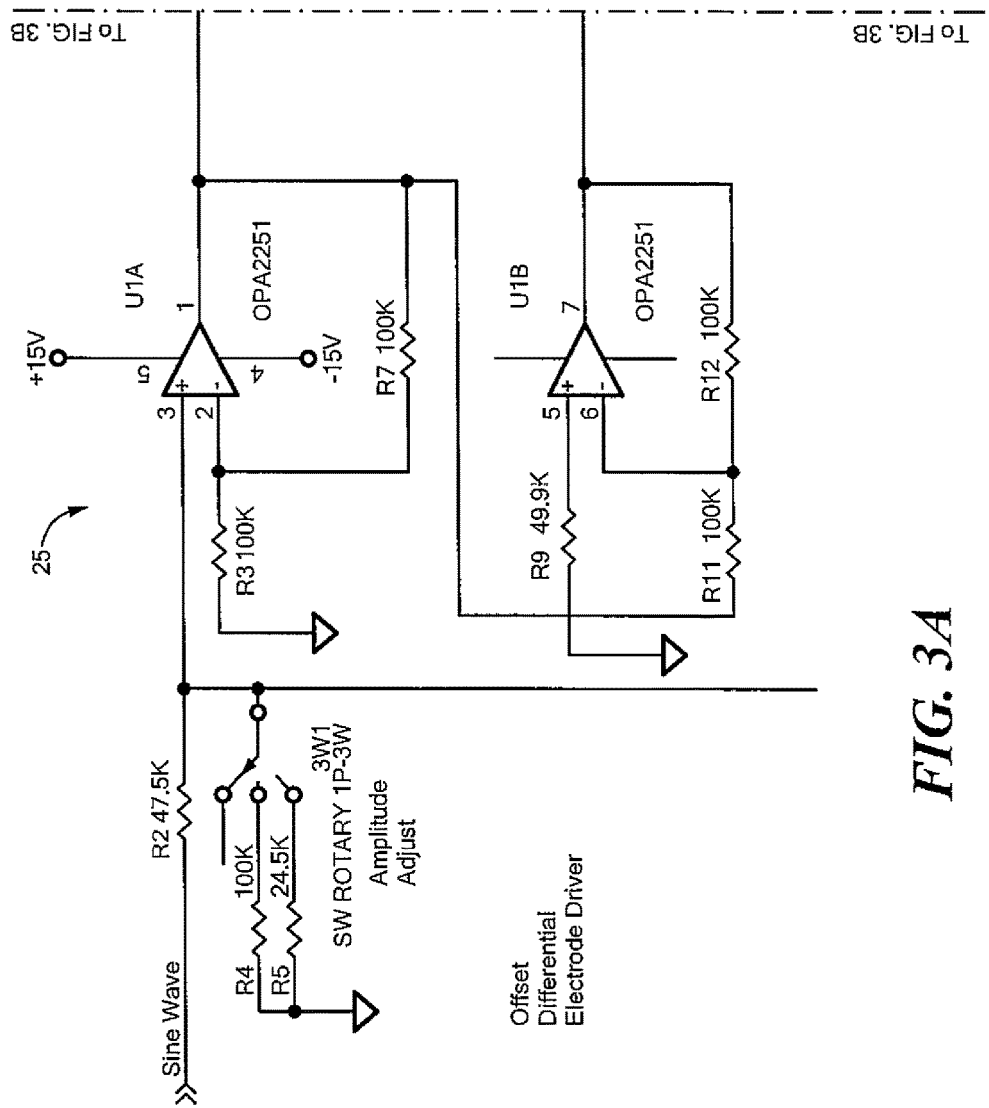
FIG. 3 shows in further detail one example of the electronics utilized by the electronics circuit board of the electronics module shown in FIGS. 1 and 2.
Figure 3B:
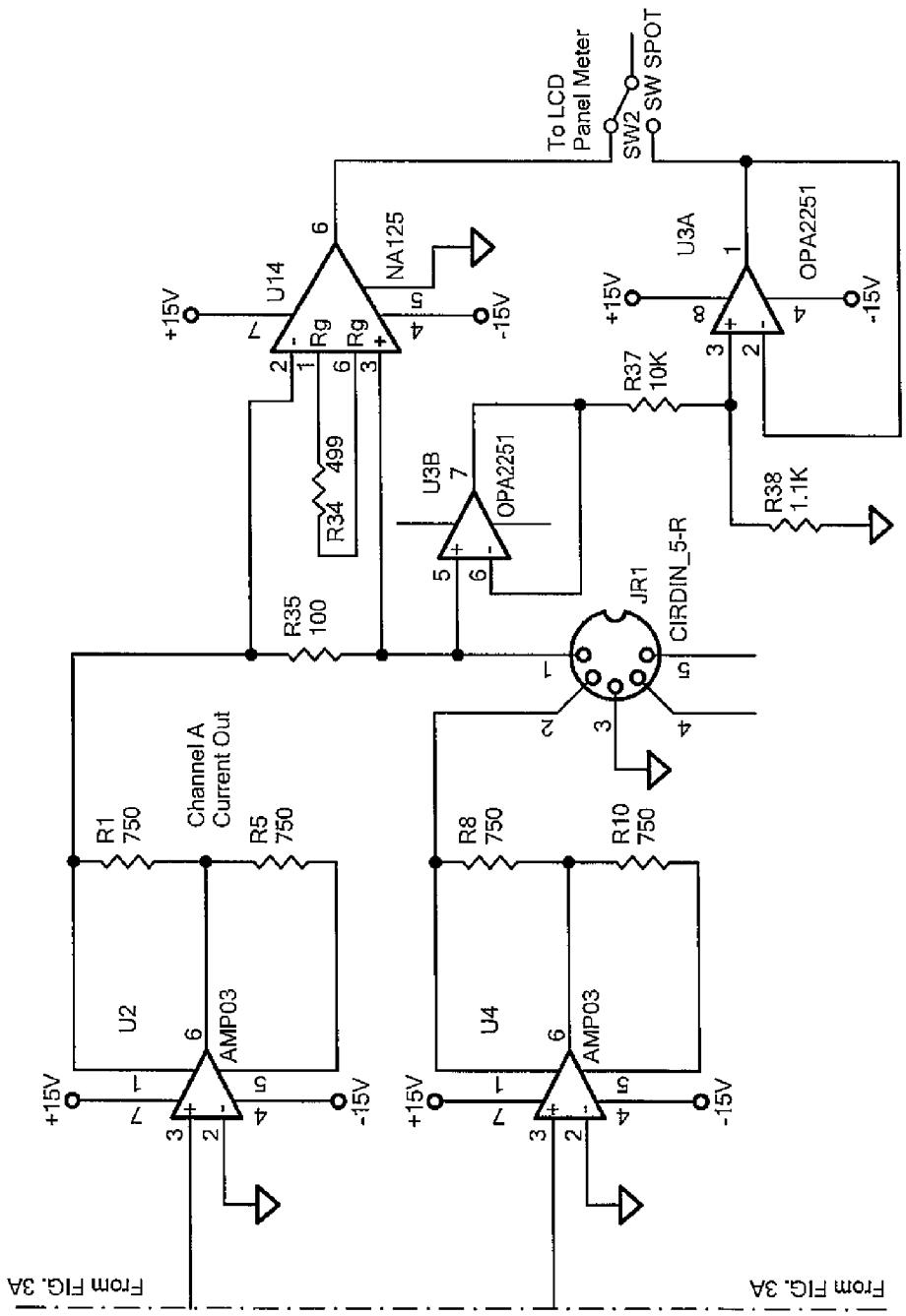
Figure 4:
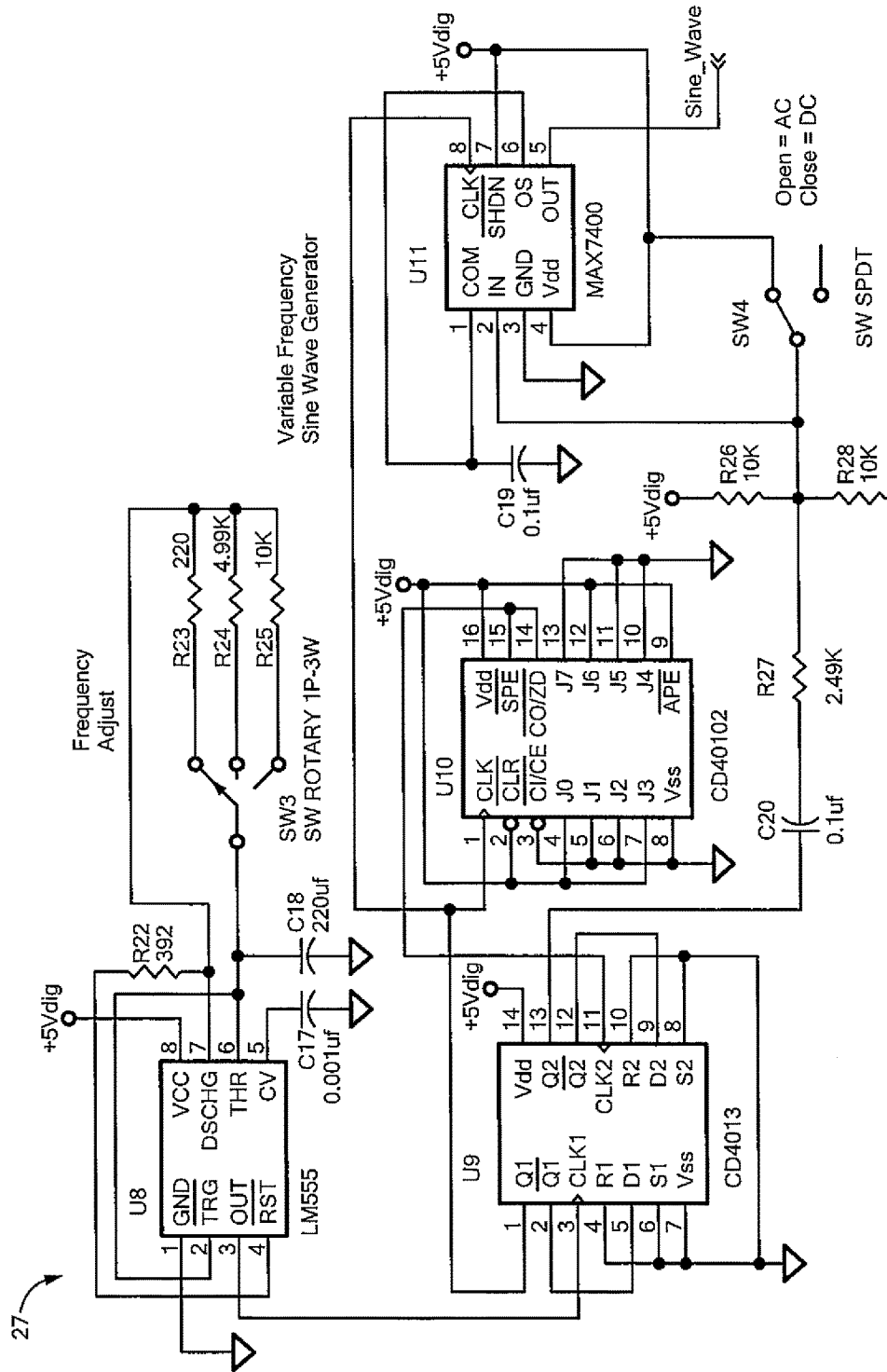
FIG. 4 shows in further detail one example of the electronics utilized by the electronics circuit board of the electronics module shown in FIGS. 1 and 2.

There is shown in FIG. 1 one embodiment for system 10 and the method thereof for suppressing vestibular activity of a human subject. System 10 includes electronics module 12 configured to generate one or more stimulation signals which are applied to electrodes at predetermined locations of head 14 of the human subject to suppress vestibular activity as will be discussed in detail below. FIG. 2 shows examples of electronics module 12 which is capable of generating the one or more electrical stimulation signals, e.g. up to about 2.5 mA in a DC mode or an AC mode with a frequency between about 300 Hz and 12 kHz using frequency control 16 and amplitude control 18. Electronics module 12 also preferably includes display 20 which displays the current and/or voltage of the one or more stimulation signals. In one design, electronics module 12 may be operated with batteries, e.g., 6 AA batteries indicated at 22. Electronics module 12 also preferably includes electronics board 24 which is coupled to frequency control 16, amplitude 18, display 20, and connectors 52. Electronics board 24 is configured to generate the one or more electrical stimulation signals. FIGS. 3 and 4 show in further detail examples of electronic circuitry 25, 27, respectively, incorporated into electronics board 24 of electronics module 12, FIGS. 1 and 2, which may be used to generate the one or more electrical stimulation signals to suppress vestibular activity.

System 10, FIG. 1, also includes a plurality of electrodes each placed proximate a predetermined location on head 14 of the human subject configured to deliver the one or more electrical stimulation signals to the predetermined location on head 14 to suppress vestibular activity. In the example shown in FIG. 1, system 10 includes plurality of electrodes 22 placed proximate a predetermined on one side of head 14 and plurality of electrodes 26 bilaterally placed proximate a predetermined location on an opposite sided of head 14 as shown, e.g., proximate the mastoid process 40, FIG. 5, and preferably within the area indicated at 42 which is located directly behind the external ear as shown. In other examples, the predetermined location on each side of head 14 may be the temporal bone, indicated at 46

Figure 6:
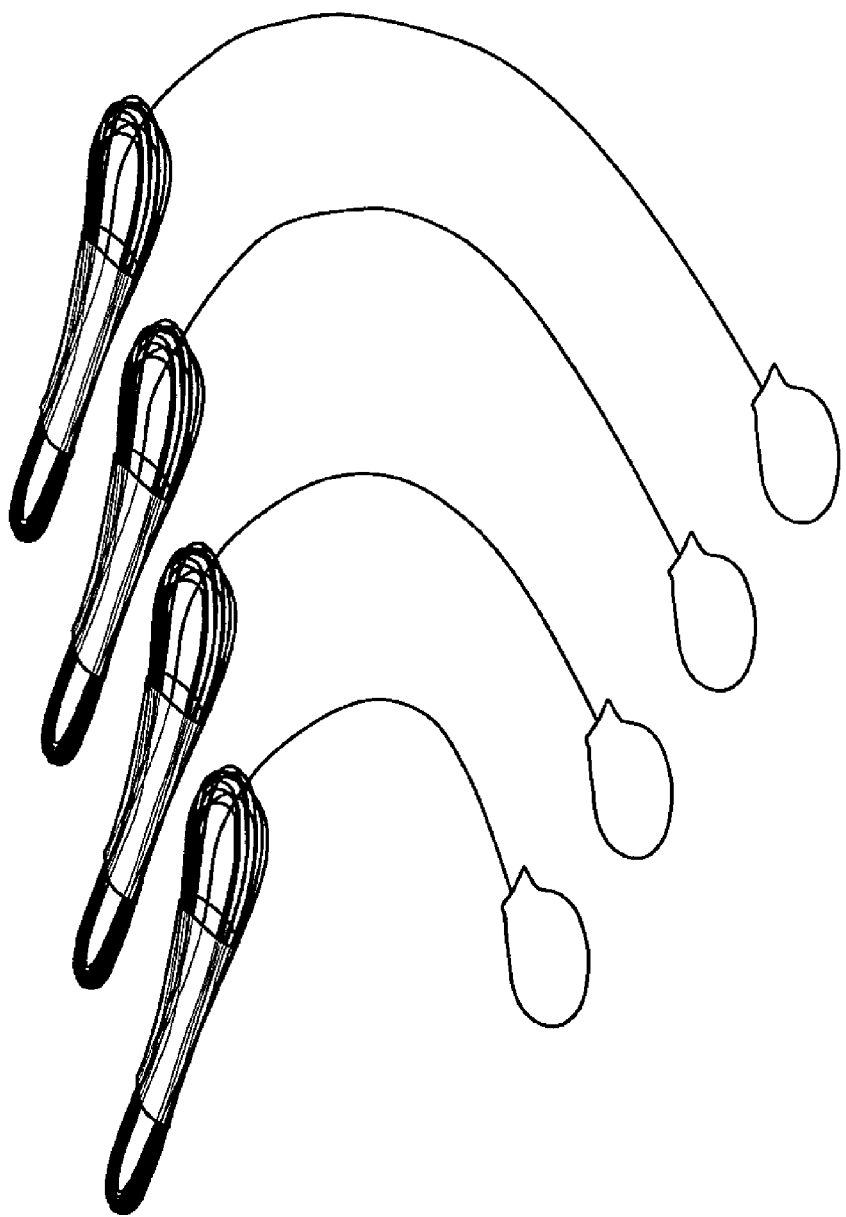
FIG. 6 shows examples of electrodes which may be utilized by the system shown in FIG. 1.

FIG. 6 shows exemplary electrodes which may be utilized (available from MFI Medical Equipment San Diego, Calif.) which are preferably coupled to connectors 52, FIG. 2.

In one example, one of the electrodes of the plurality of electrodes 22, FIG. 1, e.g., electrode 50, may be configured as a positive electrode by connecting it to contact 54 which outputs positive DC or AC current generated by electronics module 12. The other of plurality of electrodes 22, FIG. 1, e.g. electrode 54, may be configured as a negative electrode by connecting it to contact 58 which outputs negative DC or AC current generated by electronics module 12. Similarly, one of the electrodes of the plurality of electrodes 26, e.g., electrode 60, may be configured as a positive electrode by connecting it to contact 62 which outputs positive DC or AC current or voltage generated by electronics module 12 and the other of the plurality of electrodes 22, e.g., electrode 66, may be configured as a negative electrode by connecting it to negative contact 68 which outputs negative DC or AC current or voltage generated by electronics module 12. Preferably, system 10 includes ground electrode 70 preferably placed proximate the nape of the neck as shown coupled to ground contact 72.

The one or more electrical stimulation signals generated by electronics module 12 to electrodes 50, 54 on one side of head 14 at the predetermined location and the one or more electrical stimulation signals applied to electrodes 60 and 66 at the predetermined location on an opposite side of head 14 of the human subject suppresses vestibular activity.

Preferably, the vestibular system of the human subject is suppressed to actual motion by system 10 and the method thereof such that the perception of motion of the human subject is reduced. Suppression of the vestibular system of the human subject to actual motion preferably decreases motion sickness and/or SS that may arise from motion sensed by the human subject. By suppressing vestibular activity, system 10 and the method thereof may mitigate motion sickness and/or SS by reducing or eliminating the mismatch between sensory cues inputs expected by a human subject and improve simulation based training.

Figure 7:
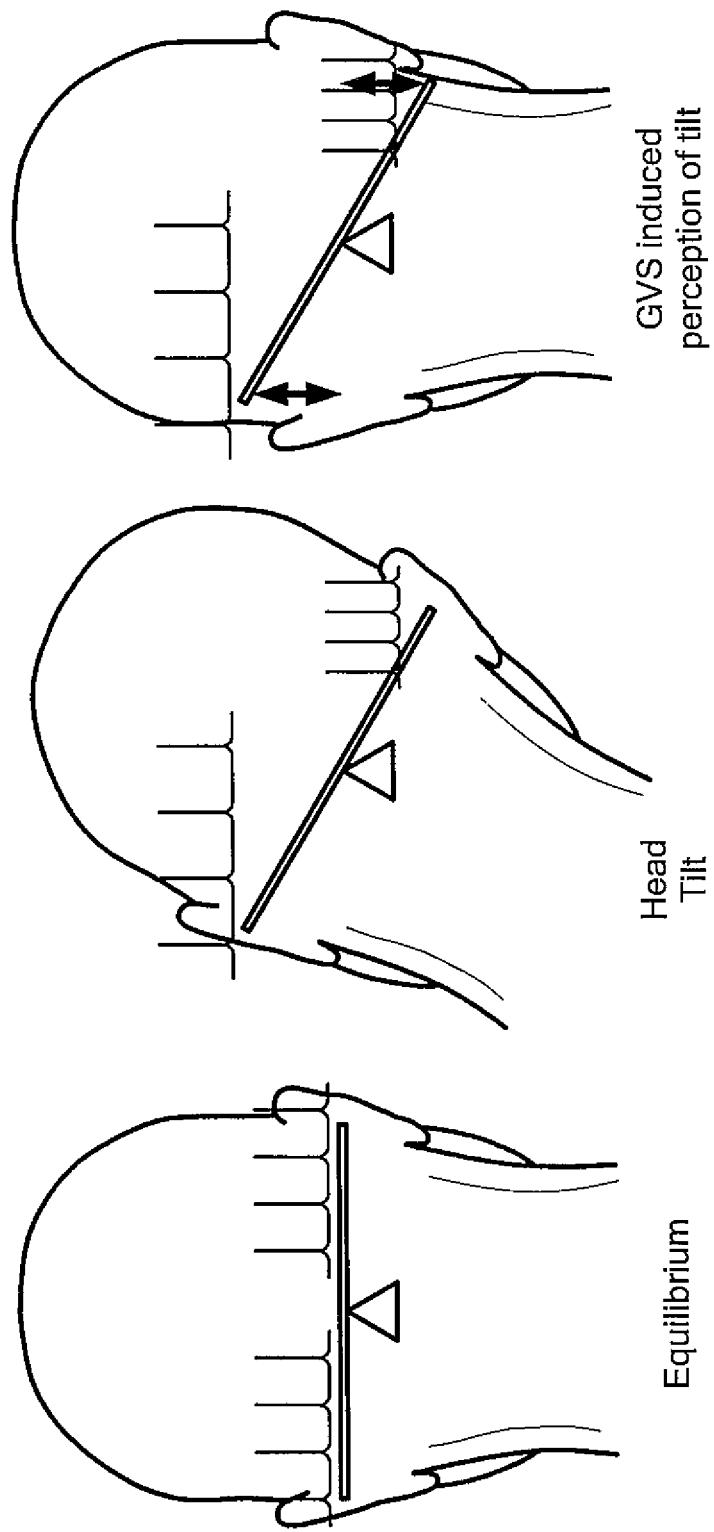
FIG. 7 shows examples of galvanic vestibular stimulation which may used to mimic the body's natural reaction to head acceleration/tilt.

The one or more electrical stimulation signals generated by electronics module 12 and delivered by electrodes 50, 54 and 60, 66 preferably hyperpolarize and/or depolarize cells proximate each predetermined location on head 14 as discussed above to create a desired induced perception of motion. System 10 and the method thereof mimics the polarization of the cells caused by motion with the application of small amounts of external electrical stimulation by the one or more electrical stimulation signals. By judicious application of the one or more electrical stimulation signals at appropriate external predetermined locations, the cells on each side of head 14 are preferably hyperpolarized and/or depolarized thereby using their natural response to create the desired signals. Unlike conventional systems and methods which may rely on swamping the signals sent the brain, system 10 and the method thereof works with the healthy vestibular system of the human subject to create a transient signal associated with acceleration of the head. Upon cessation of stimulation, the cells repolarize to their "at rest" condition within a few pulses, requiring less than a second to return to their pre-stimulation condition. See FIG. 7.

In one example, the one or more electrical stimulation signals stimulation signals generated by electronics module 12, FIGS. 1-4, to suppress vestibular activity may include one or more direct current (DC) signals, one or more DC signals with an imposed carrier waves or one or more alternating current (AC) signals.

Figure 5:
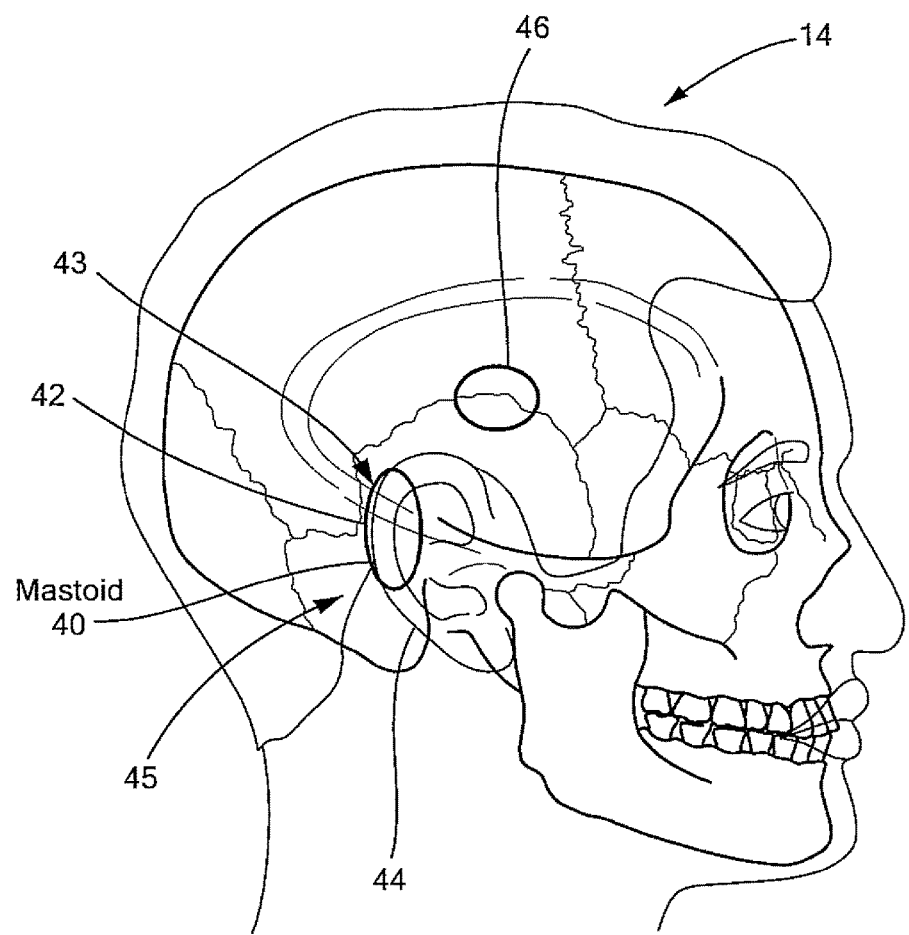
FIG. 5 shows one example of one preferred location for the placement of electrodes shown in FIG. 1 on the head of a human subject.
Figure 8:
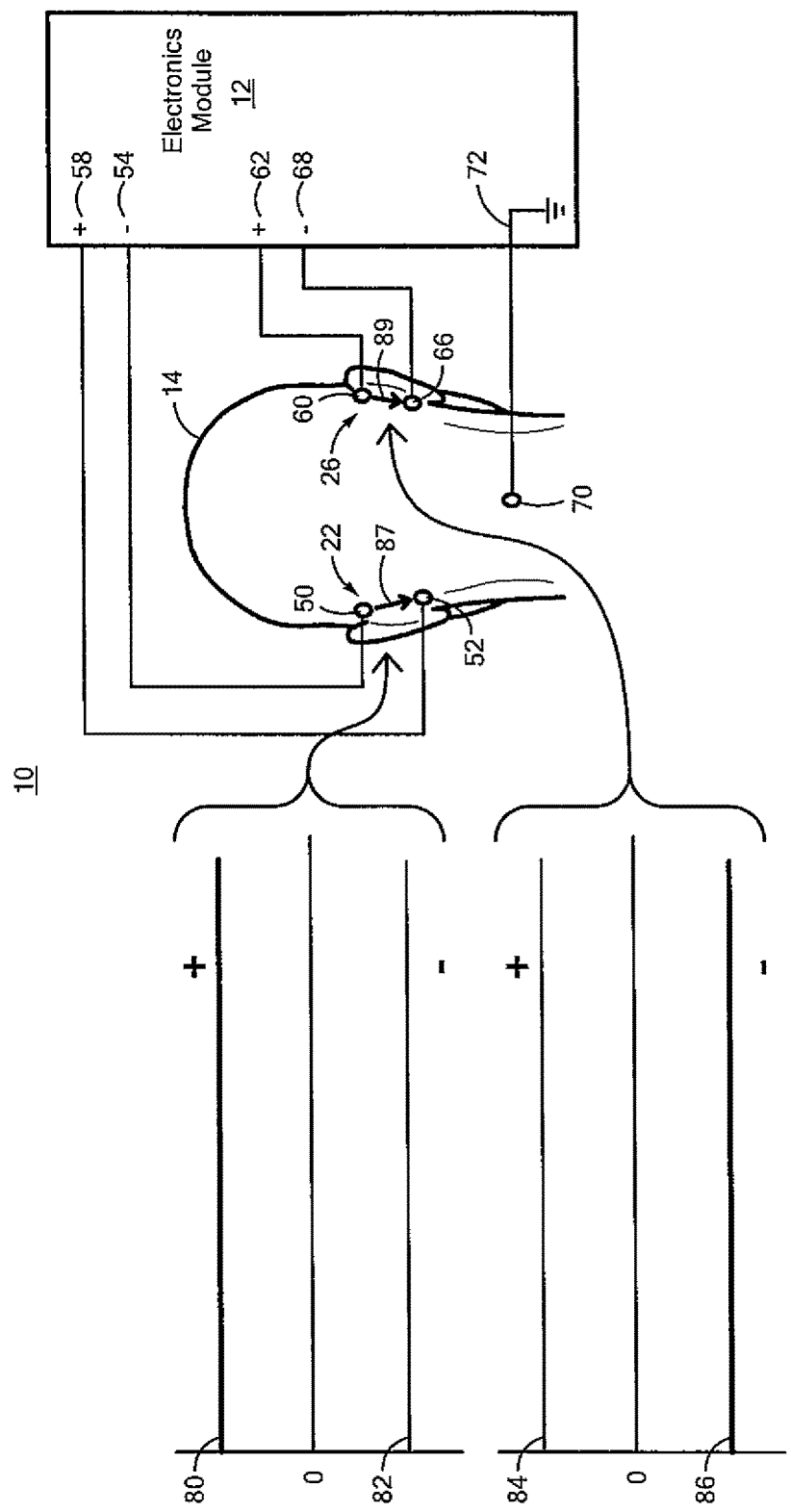
FIG. 8 is a schematic block diagram showing the primary components of another embodiment of the system for suppressing vestibular activity of a human subject.

For example, electronics module 12, FIG. 8, where like parts have been given like numbers, may generate one or more electrical stimulation signals to suppress vestibular activity configured as positive DC signal 80 which is applied electrode 50 preferably located at an upper mastoid location of the head 14 as shown, e.g., at location 43, FIG. 5 of area 42. Electronics module 12 may also generate negative DC signal 82 which is applied to electrode 52 preferably located at a lower mastoid position on the head 14 as shown, e.g., at location 45 of area 42. The one or more electrical stimulation signals in this example are transmitted from the upper mastoid location of the left side of head 14 to lower mastoid position on head 14 as shown by arrow 87 to suppress vestibular activity.

Similarly, electronics module 12 may generate one or more electrical stimulation signals to suppress vestibular activity configured as positive DC signal 84 which is applied electrode 60 preferably located at an upper mastoid location of the head 14, as discussed above. Electronics module 12 may also generate negative DC signal 86 which is applied to electrode 66 located at a lower mastoid position on the head 14 as shown, e.g., as discussed above. The one or more electrical stimulation signals in this example are transmitted from the upper mastoid location of the head 14 to lower mastoid position on the head, as shown by arrow 89, to suppress vestibular activity.

Figure 9:
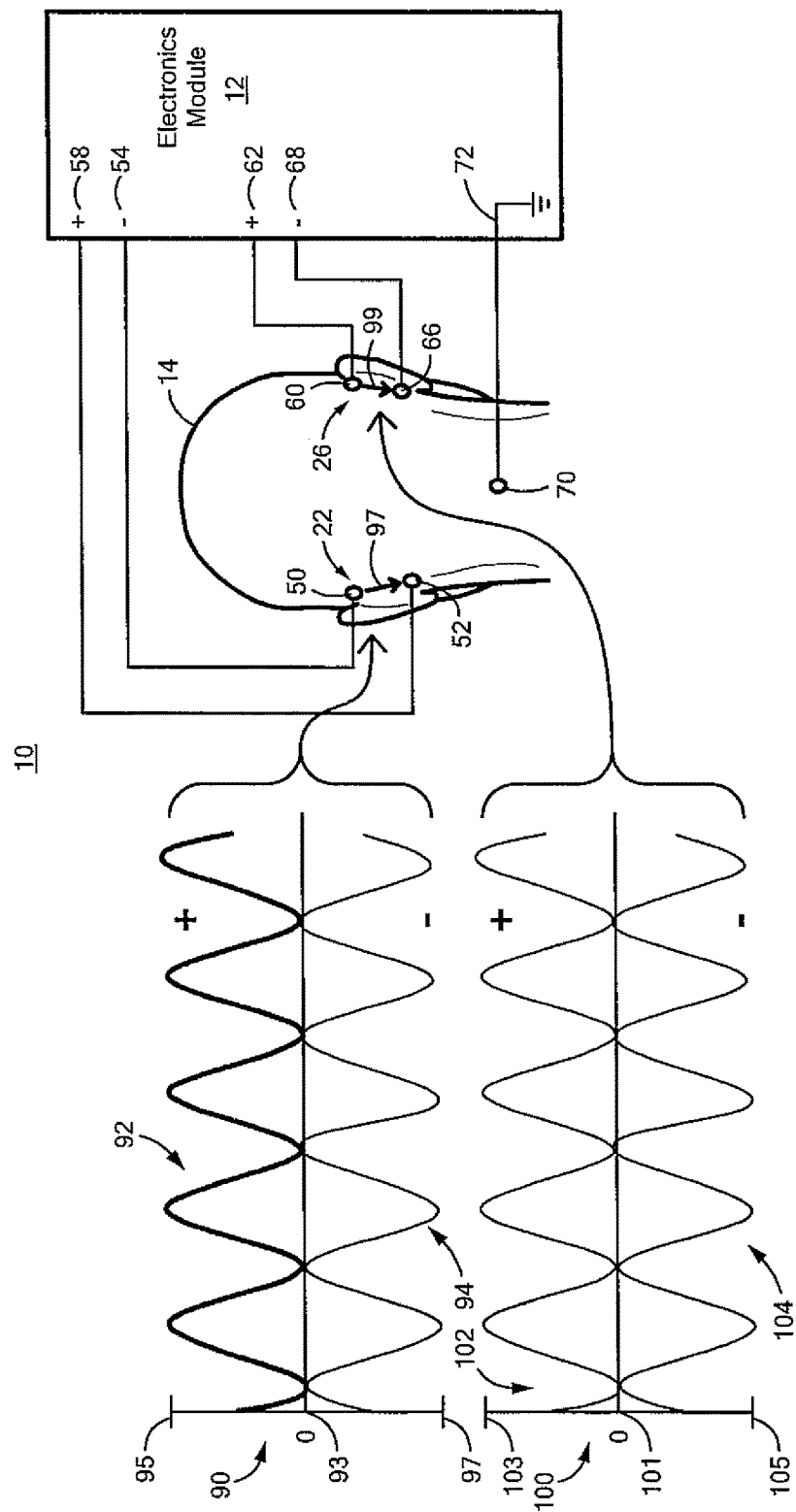
FIG. 9 is a schematic block diagram showing the primary components of another embodiment of the system for suppressing vestibular activity of a human subject.

Electronics module 12, FIG. 9, where like parts have been given like numbers, may generate one or more electrical stimulation signals to suppress vestibular activity configured as DC signal 90 with imposed positive carrier wave 92 which is applied electrode 50 preferably located at an upper mastoid location of the head 14 as shown, similarly as discussed above. Imposed carrier wave 92 modulates the current applied to electrode 50 between 0 amps, indicated at 93, and the maximum positive current, indicated at 95. Electronics module 12 may also generate DC signal 90 with imposed negative carrier wave 94 which is applied to electrode 52 located at a lower mastoid position on the head 14 as shown, similar as discussed above. Imposed negative carrier wave 94 modulates the current applied to electrode 52 between 0 amps, indicated at 95, and the maximum negative current, indicated at 97. In this example, imposed carrier waves 92 and 94 are preferably in phase such that the one or more electrical stimulation signals are transmitted from electrode 50 to electrode 52, as shown by arrow 97, to suppress vestibular activity.

Similarly, electronics module 12, FIG. 9, may generate one or more electrical stimulation signals to suppress vestibular activity configured as configured as DC signal 100 with imposed positive carrier wave 102 which is applied electrode 60 preferably located at an upper mastoid location of the head 14 as shown. Imposed positive carrier wave 102 preferably modulates the current applied to electrode 60 between 0 amps, indicated at 101, and the maximum positive current, indicated at 103. Electronics module 12, FIG. 9, may also generate DC signal 100 with imposed negative carrier wave 104 which is applied to electrode 66 located at a lower mastoid position on the head 14 as shown, as discussed above. Imposed negative carrier wave 104 modulates the current applied to electrode 66 between 0 amps, indicated at 101, and the maximum negative current, indicated at 105. In this example, carrier waves 102 and 104 are preferably in phase such that the electrical stimulation signals are transmitted from electrode 60 to electrode 66 as shown by arrow 99, to suppress vestibular activity.

Figure 10:
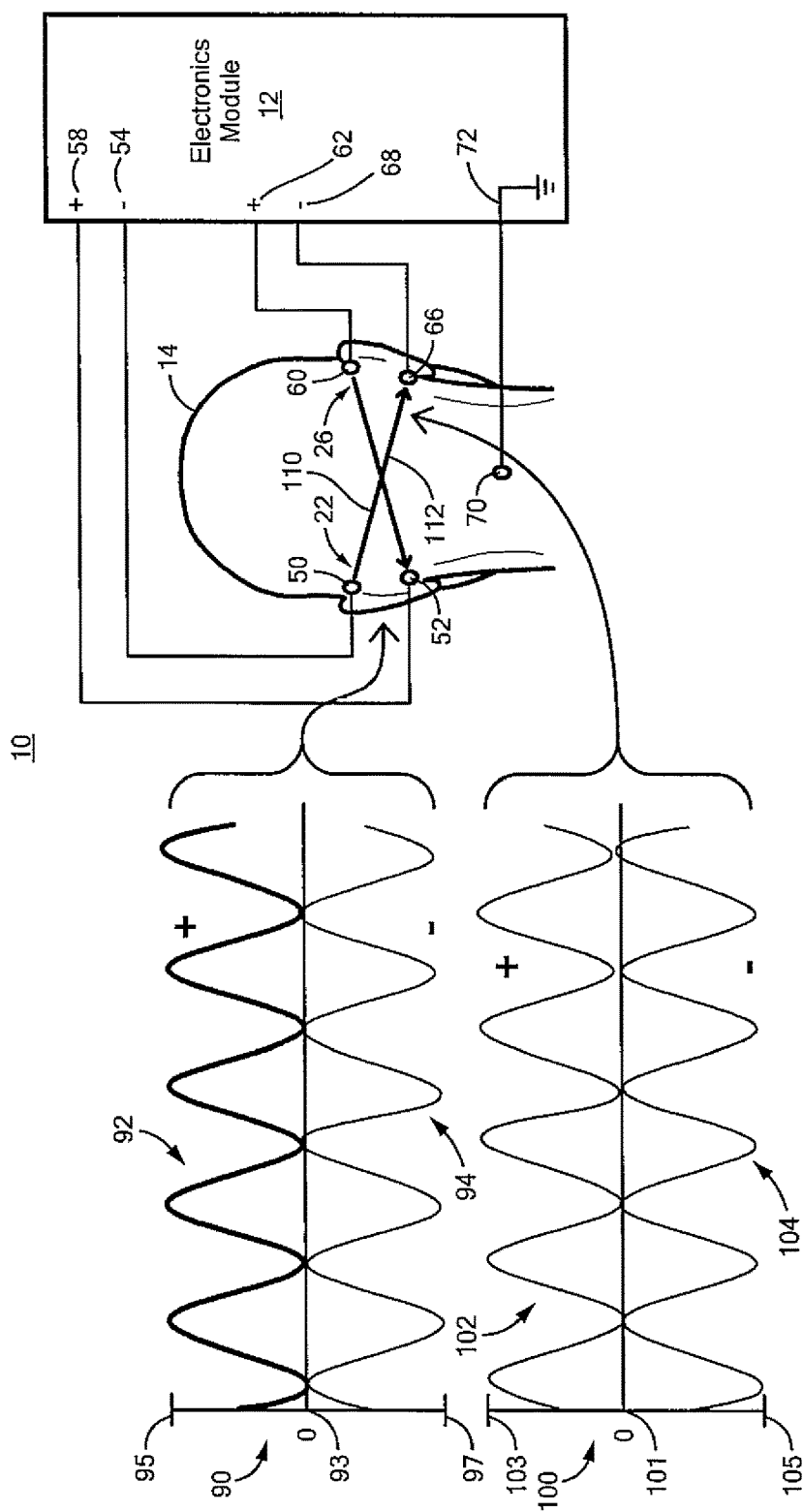
FIG. 10 is a schematic block diagram showing primary components of another embodiment of the system for suppressing vestibular activity of a human subject.

In another example, electronics module 12, FIG. 10, where like parts have been given like numbers may generate DC signal 90 with imposed carrier waves 92 and 94 which are preferably temporally offset, e.g., 180 degrees out phase, with DC signal 100 with carrier waves 102 and 104 as shown. The result is current is transmitted from electrode 50 at its maximum current on one side of head 14 at a higher mastoid position to electrode 66 at zero current on an opposite side of head 14 a lower mastoid position, as shown by arrow 110, and from electrode 60 at its maximum current on side of head 14 at a higher mastoid position to electrode 52 at zero current, on an opposite side of head 14 at a lower mastoid position, as shown by arrow 112, to suppress vestibular activity.

Figure 11:
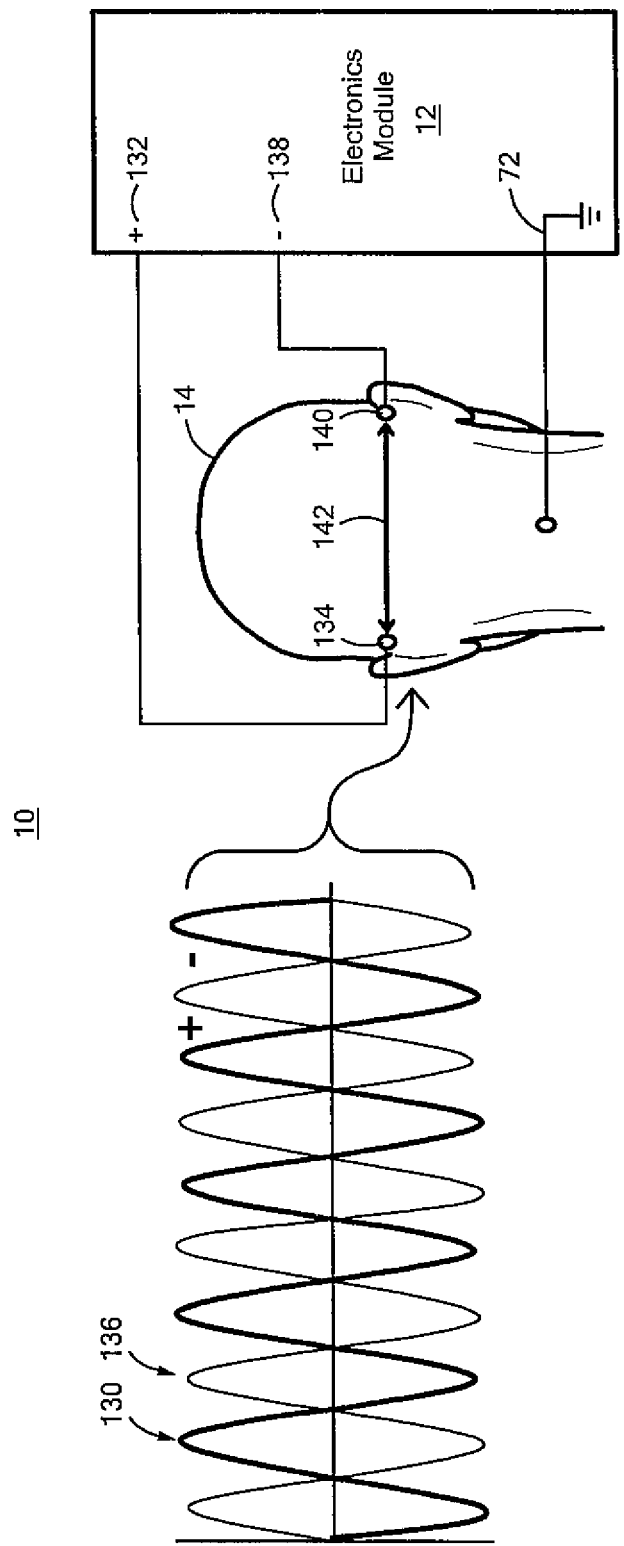
FIG. 11 is a schematic block diagram of another embodiment of the system for suppressing vestibular activity of a human subject.

Electronics module 12, FIG. 11, where like parts have been given like numbers may generate one or more electrical stimulation signals to suppress vestibular activity configured one or more AC signals. In one example, electronics module 12 preferably generates AC signal 130 by contact 132 which is applied to electrode 134 located on one side of head 14, e.g., at location 43 FIG. 5, of area 42 of the mastoid as shown, or any desired location on one side of head 14. Electronics module 12 also generates AC signal 136 by contact 138 which is temporally offset, e.g., 180 degrees out of phase, with AC signal 130. Ground electrode 70 is coupled to ground contact 72. The result is the one or more AC signals are transmitted back and forth from one of electrodes 134, 140 at its maximum positive current to one of electrodes 134, 140 and its maximum negative current, as shown by arrow 142, to suppress vestibular activity.

Figure 12:
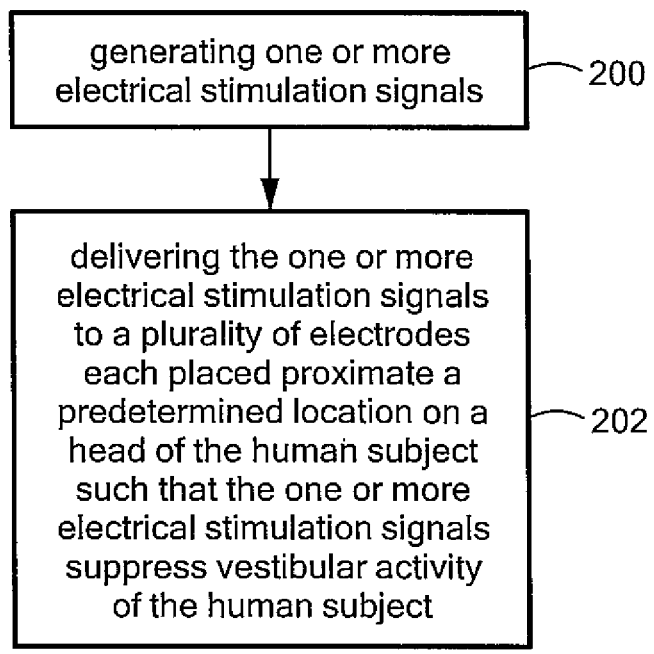
FIG. 12 is a schematic block diagram showing the primary steps associated with one embodiment of the method for suppressing vestibular activity of a human subject.

In one embodiment of the method for suppressing vestibular activity in a human subject of this invention includes generating one or more electrical stimulation signals, step 200, FIG. 12, and delivering one or more electrical stimulation signals to a plurality of electrodes each placed proximate a predetermined location on a head of the human subject such that the one or more electrical stimulation signals suppress vestibular activity of the human subject, step 202.

Although as discussed above with reference to one or more of FIGS. 8-11, the predetermined location is shown as the upper and lower mastoid, this is not a necessary limitation. In other examples, the predetermined location may be the temporal bone, the ear, or any desired location on head 14 of the human subject.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments. Other embodiments will occur to those skilled in the art and are within the following claims.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant cannot be expected to describe certain insubstantial substitutes for any claim element amended.

What is claimed is:

1. A system for suppressing vestibular activity of a human subject, the system comprising:
  an electronics module configured to generate at least first and second electrical stimulation signals, the fist electrical stimulation signal including a first carrier signal having a frequency in the range of about 300 Hz to about 12 kHz, and the second electrical stimulation signal including a second carrier signal with a frequency in the range of about 300 Hz to about 12 kHz, said first electrical stimulation signal being the first carrier signal imposed on a positive biased dc signal and said second electrical stimulation signal being the second carrier signal imposed on a negative biased dc signal;
  a plurality of electrodes each adapted to be placed proximate a predetermined location on a head of a human subject including a first electrode and a second electrode; and
  wherein the electronics module is configured to apply the first electrical stimulation signal to the first electrode while concurrently applying the second electrical stimulation signal to the second electrode to suppress vestibular activity of the human subject by hyperpolarizing and/or depolarizing cells located between said first electrode and said second electrode such that perception of motion of the human subject is reduced.

2. The system of claim 1 in which the plurality of electrodes are bi-laterally placed on opposing sides of the head.

3. The system of claim 1 in which the predetermined location includes a mastoid process of the human subject.

4. The system of claim 1 in which the predetermined location includes the ear of the human subject.

5. The system of claim 1 in which the predetermined location includes a temporal bone of the human subject.

6. The system of 1 in which the at least first and second electrical stimulation signals include one or more direct current (DC) signals.

7. The system of claim 1 in which the at least first and second stimulation signals include one or more DC signals each with an imposed carrier wave.

8. The system of claim 1 in which the at least first and second stimulation signals include one or more alternating current (AC) signals.

9. The system of claim 1 in which the at least first and second electrical stimulation signals are configured to hyperpolarize and/or depolarized cells located at each predetermined location to create a desired induced perception of motion.

10. The system of claim 1 in which the plurality of electrodes is configured to deliver electrical stimulation to suppress the vestibular system of the human subject to actual motion such that perception of motion of the human subject is reduced.

11. The system of claim 10 in which the suppression of the vestibular system of the human subject to actual motion decreases motion sickness that may arise from motion sensed by the human subject.

12. The system of claim 1 in which the plurality of electrodes includes a first pair of electrodes placed on one side of the head of the human subject at the predetermined location, another pair of electrodes placed on an opposite side of the head of the human subject at the predetermined location, and a ground electrode placed on the head or neck of the human subject.

13. The system of claim 12 in which each pair of electrodes includes an electrode configured as positive electrode and an electrode configured as a negative electrode.

14. The system of claim 13 in which the at least first and second electrical stimulation signals are configured as one or more DC signals applied to each positive and negative electrode such that the one or more DC signals are transmitted from the positive electrode located at high predetermined location on the head of the human subject to the negative electrode located at a low location on the head of the human subject to suppress vestibular activity.

15. The system of claim 14 in which the high predetermined location includes a high location on a mastoid process of the human subject and the low location includes a low location on mastoid process of the human subject.

16. The system of claim 13 in which the at east first and second electrical stimulation signals are configured as one or more DC signals each imposed carrier wave applied in phase to each positive and negative electrode such that the one or more DC signals with the imposed carrier waves are transmitted from the positive electrode at a high predetermined location to the negative electrode at a low predetermined location to suppress vestibular activity.

17. The system of claim 13 in which the at least first and second electrical stimulation signals are configured as one or more DC signals each imposed carrier wave applied temporally offset to each positive and negative electrode such that the one or more DC signals with the imposed carrier waves are transmitted from the positive electrode at a high predetermined location on one side of the head to the negative electrode at a low predetermined location on an opposite side of the head to suppress vestibular activity.

18. The system of claim 14 in which the high predetermined location includes a high location on mastoid process and the low predetermined location includes a low location on mastoid process of the human subject.

19. The system of claim 1 in which the plurality of electrodes include one electrode placed on one side of the head of the human subject at the predetermined location and another electrode is placed on an opposite side of the head of the human subject at the predetermined location.

20. The system of claim 19 in which the at least first and second electrical stimulation signals are configured as one or more AC signals applied to the electrode placed on one side of the head and the electrode placed on one the opposite side of the head such that the one or more AC signals are transmitted back and forth from one electrode at its maximum current at the predetermined location on one side of the head to the another electrode at its maximum negative current at the predetermined location on an opposite side of the head of the human subject to suppress vestibular activity.

21. A method for suppressing vestibular activity of a human subject, the method comprising:
placing at least a first and a second electrode on opposing sides of a predetermined location on a head of the human subject;
generating at least first and second electrical stimulation signals, the first electrical stimulation signal including a first carrier signal with a frequency in the range of about 300 Hz to about 12 kHz and the second electrical stimulation signal including a second carrier signal with a frequency of about 300 Hz to about 12 kHz, said at least first electrical stimulation signal being the first carrier signal imposed on a positive biased dc signal and said at least second electrical stimulation signal being the second carrier signal imposed on a negative biased dc signal; and
delivering the at least first electrical stimulation signal to at least said first electrode and the at least second electrical stimulation signal to the at least said second electrode such that the at least first and second electrical stimulation signals suppress vestibular activity of the human subject.

22. The method of claim 21 further including bilaterally placing the at least first and second electrodes on opposing sides of the head of the human subject at the predetermined location.

23. The method of claim 21 in which the at least first and second electrical stimulation signals hyperpolarize and/or depolarize cells located at each predetermined location to create a desired induced perception of motion.

24. The method of claim 21 further including delivering the at least first and second electrical stimulation signals to suppress the vestibular system of the human subject to actual motion such that perception of motion of the human subject is reduced.

25. The method of claim 24 in which the suppression of the vestibular system of the human subject to actual motion decreases motion sickness that may arise from motion sensed by the human subject.

26. The method of 21 in which the at least first and second electrical stimulation signals include one or more of: one or more direct current (DC) signals, one or more DC signals each with an imposed carrier wave, and one or more alternating current (AC) signals.

27. The method of claim 21 in which the at least first and second electrical stimulation signals include one or more DC signals transmitted from a positive electrode at a high predetermined location on one side of the head to the negative electrode at a low predetermined location on an opposite side of the head to suppress vestibular activity.

28. The method of claim 21 in which the at least first and second electrical stimulation signals include one or more DC signals with the imposed carrier waves transmitted in phase from a positive electrode at a high predetermined location on one side of the head to the negative electrode at a low predetermined location on an opposite side of the head to suppress vestibular activity.

29. The method of claim 21 in which the at least first and second electrical stimulation signals include one or more DC signals with the imposed carrier waves transmitted temporally offset from a positive electrode at a high predetermined location on one side of the head to the negative electrode at a low predetermined location on an opposite side of the head to suppress vestibular activity.

30. The method of claim 21 in which the at least first and second electrical stimulation signals include one or more AC signals transmitted from an electrode on one side of the head at the determined location to an electrode on an opposite side of the head to suppress vestibular activity.

* * * * *

UNITED STATES PATENT AND TRADEMARK OFFICE
CERTIFICATE OF CORRECTION

Page 1 of 1

PATENT NO. : 10,207,101 B2
APPLICATION NO. : 15/079445
DATED : February 19, 2019
INVENTOR(S) : Anna M Galea et al.

It is certified that error appears in the above-identified patent and that said Letters Patent is hereby corrected as shown below:

In the Specification

Column 1, Line 7 reads "No. W56HZV-13-C-0036, awarded by the U.S. Army. The" Should read "No. W56HZV-12-C-0010, awarded by the U.S. Army. The"

Signed and Sealed this
Nineteenth Day of October, 2021

Drew Hirshfeld
*Performing the Functions and Duties of the*
*Under Secretary of Commerce for Intellectual Property and*
*Director of the United States Patent and Trademark Office*